United States Patent [19]

Scott et al.

[11] 4,383,525

[45] May 17, 1983

[54] IMPLANTABLE PENILE PROSTHETIC CYLINDER WITH INCLUSIVE FLUID RESERVOIR

[75] Inventors: F. Brantley Scott, Houston, Tex.; John H. Burton, Minnetonka, Minn.

[73] Assignee: American Medical Systems, Inc., St. Louis Park, Minn.

[21] Appl. No.: 264,202

[22] Filed: May 15, 1981

Related U.S. Application Data

[63] Continuation-in-part of Ser. No. 108,124, Dec. 28, 1979, Pat. No. 4,267,829.

[51] Int. Cl.³ .............................................. A61F 5/00
[52] U.S. Cl. ............................................ 128/79; 3/1
[58] Field of Search ................................. 128/79; 3/1

[56] References Cited

U.S. PATENT DOCUMENTS

| | | | |
|---|---|---|---|
| 3,853,122 | 12/1974 | Strauch et al. | 128/79 |
| 3,954,102 | 5/1976 | Buuck | 128/79 |
| 4,009,711 | 3/1977 | Uson | 128/79 |
| 4,201,202 | 5/1980 | Finney et al. | 3/1 X |
| 4,267,829 | 5/1981 | Burton et al. | 128/79 |

Primary Examiner—John D. Yasko
Attorney, Agent, or Firm—Williamson, Bains, Moore & Hansen

[57] ABSTRACT

A surgically implantable prosthesis for the treatment of penile erectile impotence in male patients. The device comprises at least one elongated cylinder implanted within one of the corpora cavernosa of the penis. The flexible, distal end of the cylinder is adapted to rigidize upon being filled with pressurizing fluid. The rear tip or proximal end of the cylinder is formed to provide a chamber which serves as a fluid reservoir. Valve means contained within the cylinder controls fluid flow between the rear tip reservoir and the flexible, distal end of the cylinder. The prosthesis further includes a manually operable pump means utilized to transfer pressurized fluid from the rear tip reservoir to the distal end of the cylinder in order to achieve an erection. The walls of the rear tip reservoir itself may serve as the pump means; or a separate pump may be implanted within the scrotum.

12 Claims, 9 Drawing Figures

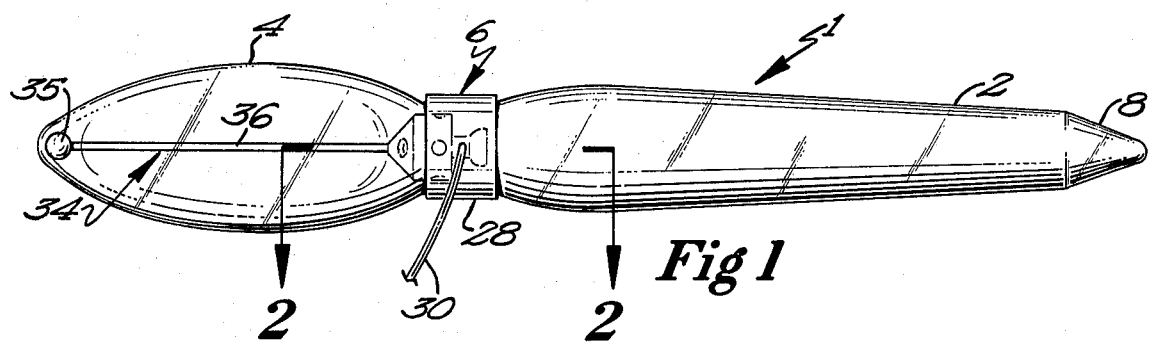
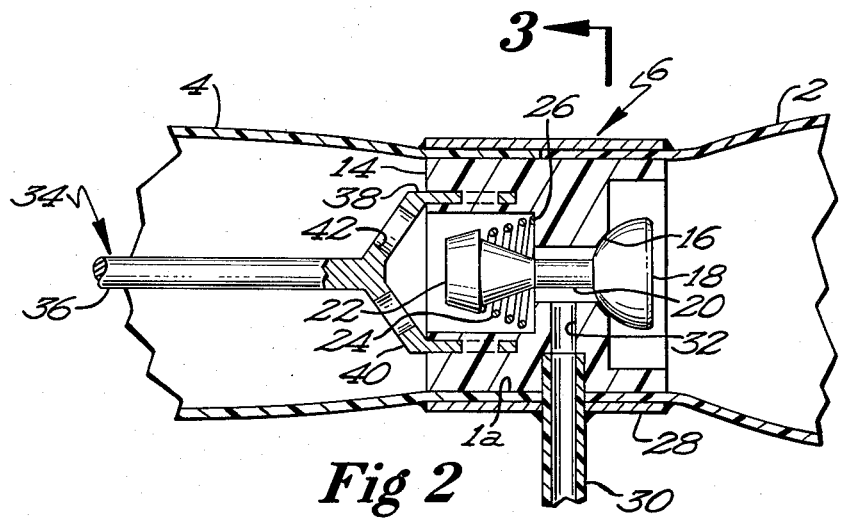
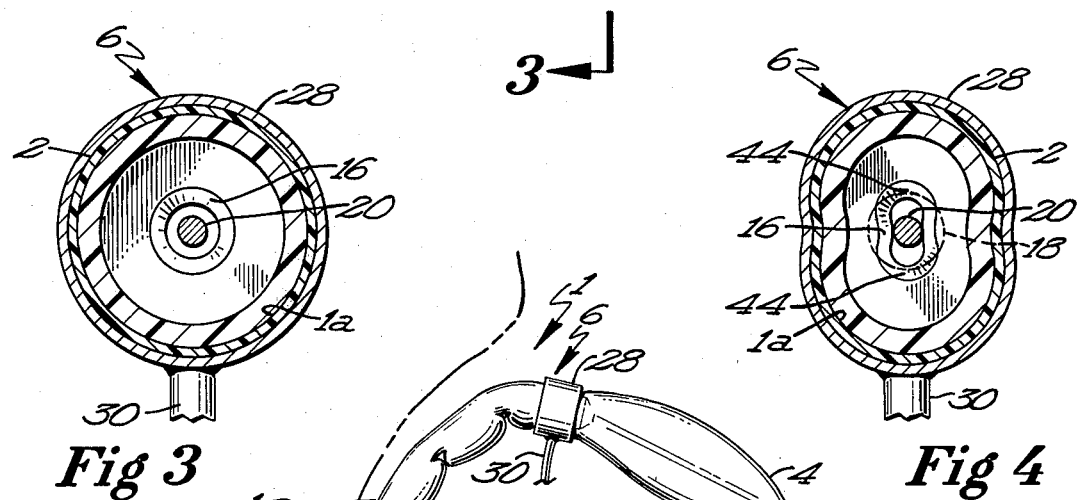
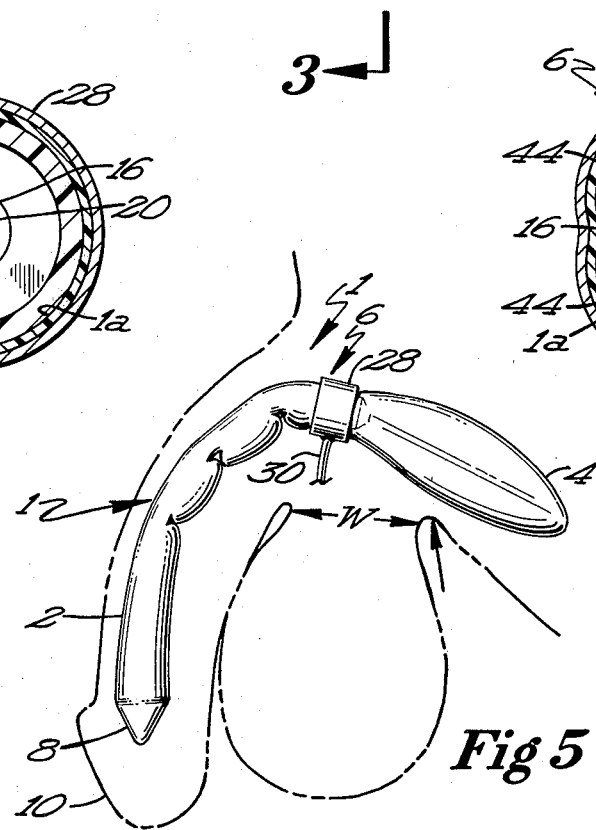

IMPLANTABLE PENILE PROSTHETIC CYLINDER WITH INCLUSIVE FLUID RESERVOIR

BACKGROUND OF THE INVENTION

This is a continuation-in-part of U.S. application No. 108,124 filed Dec. 28, 1979, entitled PENILE PROSTHESIS, and now issued as U.S. Pat. No. 4,267,829.

This invention relates generally to the field of implantable medical prosthetic devices for treating male erectile impotence, and more particularly to penile prosthetic implants operated by fluid pressure supplied from an implanted pump device.

Implantable penile prostheses for the management of erectile impotence utilizing inflatable cylinders which are implanted within the penis are described and disclosed by Scott et al in *Urology*, Vol. II, No. 1, July 1973, pp. 80–82; and by Kothari et al in the *Journal of Biomechanics*, Vol. V, 1972, pp. 567–570. The prosthetic devices disclosed in those articles comprise a reservoir to hole a radiopaque fluid used to activate the device through inflatable cylinders adapted to be placed inside of the corpora cavernosa of the penis, and two pumping mechanisms for inflating and deflating the cylinders. The inflatable cylinders are disclosed as comprising collapsible tubes constructed of dacron reinforced silicone rubber and having a shape simulating the corpora cavernosa. Valves are employed in the disclosed fluidic system in such a way as to permit selective actuation of the pumping mechanisms to inflate and deflate the cylinders. In this manner, the patient is able to selectively produce an erection and to return the penis to a flaccid state by manual manipulation of the pumping mechanisms.

A method and device for achieving a penile erection is described by Strauch et al in U.S. Pat. No. 3,853,122. That patent discloses an elongated, flexible, and stretchable hollow tube implanted in the penis. A flexible, fluid container is provided for implantation in the scrotum or in the lower abdomen of the patient. Pressing on the implanted container serves to displace the fluid into the tube to render the tube relatively rigid, thus providing the desired erection.

Another penile prosthesis for the management of erectile impotence is described by Uson in U.S. Pat. No. 4,009,711. Uson shows a body member having a nondistensible portion and a distensible body portion, with the latter being connected by suitable conduit means to a fluid supply source implanted within the patient. The nondistensible portion is preferably made of plastic material, such as Silastic, which is relatively rigid and is adapted to be implanted into the root end of the corpus cavernosum of the penis to anchor the prosthetic device in place. The distensible body portion is connected by fluid conduit means to a pump bulb implanted within the scrotum. The Uson prosthesis is thus rigid at the root of the penis, and inflatable at the pendulous portion of the penis.

The penile erection system disclosed by Buuck in U.S. Pat. No. 3,954,102 is an improved variation of that disclosed in the aforesaid Scott et al and Kothari et al articles. The Buuck patent discloses a pair of inflatable and collapsible cylinders adapted to be implanted within the corpora cavernosa of the penis and to simulate their function. Each cylinder includes a cylindrical silicone rubber body or sleeve which is expansible circumferentially and also longitudinally. A single pump bulb implanted within the scrotum is utilized to selectively deliver fluid to the inflatable cylinders through a valve system. A separate, fluid reservoir implanted within the abdomen of the male patient contains the fluid utilized to activate the inflatable cylinders. Pumping of the squeeze bulb within the scrotum serves to transfer fluid from the reservoir to the cylinders. A manually actuable bypass valve contained within the pump bulb implanted within the scrotum is manipulated to permit pressurized fluid to flow from the cylinders back to the fluid reservoir in order to return the penis to a flaccid state.

Prior art inflatable penile prostheses as implanted and used in actual practice have required relatively large fluid reservoirs as disclosed in the Buuck patent to contain the amount of fluid necessary to inflate elongated, stretchable hollow tubes implanted in the penis. It is disadvantageous to implant a large fluid reservoir in the scrotum. It is also undesirable to implant separate structures, such as a fluid reservoir and connecting fluid conduits, at remote locations from the penis or from a pump device implanted in the scrotum. Such fluidic systems complicate the surgical implant procedure. One approach to simplifying the implantable prosthesis, particularly with respect to the fluid pressurizing system, is disclosed in the aforesaid U.S. application Ser. No. 108,124, of which this application is a continuation-in-part. In that copending application, there is disclosed a pressurizable implant cylinder which is comprised of a substantially rigid front or distal portion, a rigid rear portion for mounting inside the root end of the penis, and a tubular section attached to and mounted between the front and rear portions so as to define a chamber which is connected to pump means. The tubular section is collapsible but resists stretching so that the volume of the chamber undergoes only a small change as the penis is caused to go between a nonerect, bent condition and an erect condition. Therefore, only a small volume of fluid is required to actuate the cylinder to an erect, rigid condition. The pump means as disclosed in the aforesaid application may take the form of a separate pump bulb implanted within the scrotum or a fluid chamber formed within the distal end of the implantable cylinder to provide a fully self-contained implantable prosthesis.

The implantable penile prosthesis of this invention reflects a further improvement and variation of a fluid pressurized prosthetic device with a simplified fluidic system which does not require a separate fluid reservoir implanted in the abdomen or other remote location.

BRIEF SUMMARY OF THE INVENTION

This invention is directed to an implantable penile prosthesis of the fluid operated type. A flexible, fluid pressurizable, cylinder adapted to be implanted within the corpus cavernosum along the distal end of the penis is combined with a fluid reservoir, pump means and control valve in a compact fluidics arrangement which greatly simplifies the implant surgery required and reduces associated risk and patient discomfort.

A further object is to provide such a simplified penile prosthesis for treatment of male impotence which permits the patient to readily manipulate the pump and control valve to selectively produce an erection or maintain the penis in a nonerect, flaccid state.

This invention also has as an objective the provision of an implantable penile prosthesis which may be implanted, in part, in the scrotum but which does not occupy so much of the intrascrotal space as to interfere with the functioning of bodily organs contained therein or cause patient discomfort.

It is a further object to provide an implantable penile prosthesis of the aforesaid type which does not require the surgical implantation of components of the fluidics system at locations remote from the penis.

These basic objectives are realized by an implantable penile prosthesis comprised of an elongated cylinder adapted to be preferably implanted within the corpus cavernosum of the penis, with the cylinder including a fluid pressurizable distal end section and a self-contained fluid reservoir chamber formed within one end thereof. A valve mechanism for controlling the flow of fluid back and forth between the reservoir chamber and the distal end of the cylinder is also contained within the cylinder. The prosthesis further comprises pump means manually operable to transfer fluid under pressure from the reservoir chamber to the distal end of the cylinder implanted within the distal or pendulous end of the penis for producing an erection.

Preferably, the proximal, rear or root end section of the cylinder is formed to provide the fluid reservoir chamber. In one preferred embodiment, the reservoir chamber within the implant cylinder also serves as the pump means. The walls of the rear end section of the cylinder forming the fluid reservoir are resiliently compressible; and, upon implantation, are accessible for direct manual pumping action through the patient's perineal tissue. The aforesaid valve mechanism is positioned within the implant cylinder so that upon implantation it will be located within the penis where it will be accessible for manual actuation. Unseating the control valve through manual pressure permits the return flow of fluid to the fluid reservoir chamber from the distal section of the implant cylinder for returning the penis to a flaccid state.

In an alternative version of the prosthesis, the pump means comprises an elastomeric bulb adapted to be implanted within the scrotum. The pump bulb is in fluid flow communication with the aforesaid reservoir chamber and distal end section of the implant cylinder through the valve mechanism contained within the cylinder. In this embodiment, the valve mechanism comprises check valves which function to permit fluid flow from the reservoir chamber to the distal end section of the cylinder as the pump is actuated through the scrotal skin. Connector means between the pump bulb and the valve mechanism allows the check valves to be unseated for returning fluid to the reservoir chamber from the distal end section of the cylinder, by manual manipulation of the pump bulb through the scrotal skin.

These and other objects and advantages of the invention will be readily understood as the following description is read in conjunction with the accompanying drawings wherein like reference numerals have been used to designate like elements throughout the several views.

BRIEF DESCRIPTION OF THE DRAWINGS

FIG. 1 is a top, plan view of one preferred embodiment of the penile prosthesis of this invention;

FIG. 2 is a fragmentary, section view showing the valve chamber and interconnecting portions of the penile prosthesis cylinder, taken along lines 2—2 of FIG. 1;

FIG. 3 is a section view of the valve mechanism of FIG. 1 taken along lines 3—3 of FIG. 2;

FIG. 4 is a section view of the valve mechanism taken at the same location on FIG. 2 as is the view for FIG. 3, but showing the valve seat displaced to open the valve;

FIG. 5 is a side elevation view showing the penile prosthesis of FIG. 1 implanted in a male with the prosthesis in a nonerect condition and wherein portions of the male anatomy including the penis and scrotum are shown in phantom;

DESCRIPTION OF THE PREFERRED EMBODIMENT

Figures 6, 7, 8, 9:
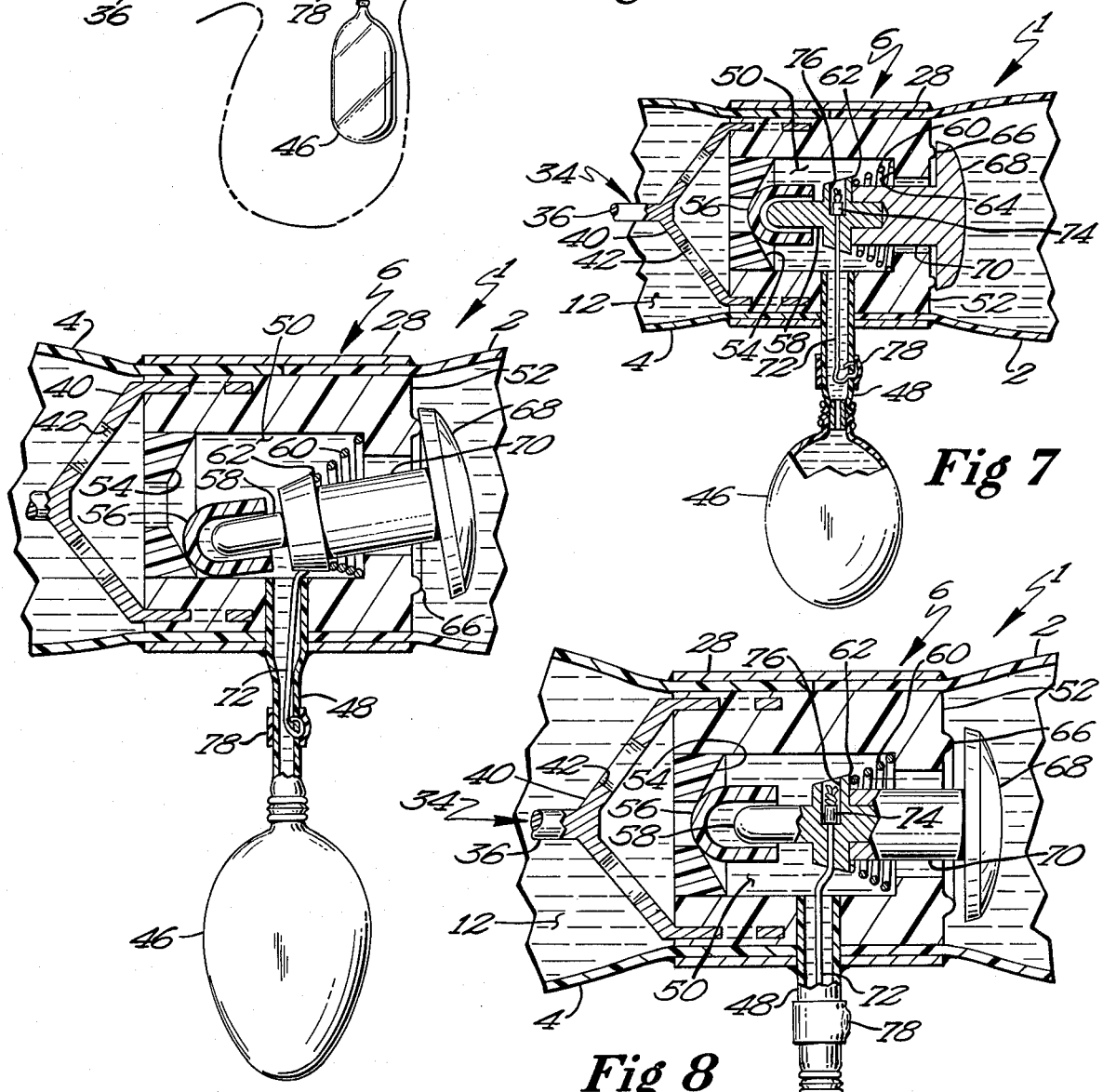
FIG. 6 is a side elevation view showing an alternative embodiment of the penile prosthesis as implanted in a male patient, with the prosthesis in an erect condition.
FIG. 7 is a section view showing the valve mechanism of the embodiment of the penile prosthesis depicted in FIG. 6, taken along lines 7—7 of FIG. 6.
FIG. 8 is a section view showing the same valve mechanism as depicted in FIG. 7, but with the valves depicted in their pumping stroke positions with fluid flowing from the pump to the distal end of the implant cylinder.
FIG. 9 also shows the same cross section view of the valve assembly as depicted in FIGS. 7 and 8, but with the valve assembly actuated to the position which it will assume to permit reverse flow of fluid from the distal cylinder to the fluid reservoir.

Referring now to the drawings, there is shown in FIGS. 1 through 5 one preferred embodiment of the implantable penile prosthesis. The prosthesis is comprised of an elongated cylinder generally indicated by reference numeral 1. Cylinder 1 is adapted to be implanted within the patient's penis, and preferably within one of the corpus cavernosum of the penis. Cylinder 1 is comprised of a distal end section 2 and a proximal or root end section 4 separated by a valve section generally indicated by reference numeral 6. Distal end section 2 is flexible and is adapted for implantation within the pendulous segment of the penis. To that end, distal section 2 is tapered along its length from a point adjacent its end near valve section 6 towards its distal tip. This shape conforms generally to the tapered shape of the corpora cavernosa of the penis. More sharply tapered tip 8 is adapted to be positioned under the glans 10 of the penis as shown in FIG. 5. Thus, though the tubular prosthetic insert 1 is generally referred to as a cylinder, it is to be understood that the distal end section 2 of the cylinder is preferably tapered as described herein.

Distal end section 2 is formed from a medical grade, biocompatible material which will permit it to flex and bend, whereby the penis may assume a bent, nonerect condition as shown in FIG. 5; however, the construction of distal section 2 is such that it will be impervious to fluid, and will rigidize upon being filled with a pressurizing fluid so as to permit the penis to assume an erected state.

As may be noted most clearly by reference to FIGS. 1 and 2, distal section 2 and proximal section 4 of the implant device 1 are preferably formed from the same material joined together within valve section 6 at a sealed joint as by gluing to form a continuous tubular implant device 1. Proximal, root section 4 of the implant device is formed to provide a fluid reservoir chamber indicated by reference numeral 12 in FIG. 2. Thus, in this manner, the reservoir chamber for pressurizing fluid is self-contained within the body of generally cylindrical prosthetic implant device 1. When implanted within a male patient as shown in FIG. 5, proximal reservoir chamber section 4 of implant 1 will be positioned in the root segment of a corpus cavernosum. This location ensures the accessibility of reservoir chamber proximal section 4 for manual manipulation when it also serves as a pump as hereinafter set forth.

Also contained within the implant cylinder 1 is a valve section generally indicated by reference numeral 6. This valve section as shown in FIGS. 2-4 includes a valve block 14 which may be made of hard rubber, such as medical grade silicone. In the embodiments shown herein, valve block 14 is positioned within cylinder 1 between fluid reservoir chamber 12 and distal end section 2 of implant device 1. It is formed to include a valve seat 16 with which a valve poppet or element 18 cooperates to provide a fluid flow control function between reservoir chamber 12 and distal end section 2. Valve poppet 18 is connected by a stem 20 to a valve head 22. A coil spring 24 is positioned as shown between annular shoulder 26 of valve block 14 and valve head 22 so as to normally urge valve poppet 18 to the left as viewed in FIG. 2 in a closing position against seat 16. Valve block 14 is hollow internally so as to provide a chamber accomodating the aforesaid valve components.

The valve section 6 and the joint between cylinder sections 2 and 4 of the implant cylinder 1 are preferably reinforced and sealed by a band or ring 28 made of the same silicone or polyurethane material of which cylinder 1 is constructed. A charging tube 30 extends through reinforcing band 28 and the wall 1a of cylinder 1 surrounding valve block 14 and connects with an internal flow passage 32. Tube 30 serves for initially charging fluid into cylinder 1 for containment within reservoir chamber 12 and distal end section 2. The fluid with which cylinder 1 is charged will be a biocompatible, preferably radiopaque liquid, such as a saline solution which is noncompressible.

A one piece stiffener generally indicated by reference numeral 34 is positioned within the walls of cylinder 1 defining proximal, root section 4 forming reservoir chamber 12. Stiffener 34 is preferably made from stainless steel and includes a rod 36 extending between a rounded end 35 and a continuous skirt head comprised of a conical segment 40 and a cylindrical skirt 38. Skirt 38 is imbedded within the rubber forming valve block 14 and is apertured as shown for secure retention within the silicone rubber from which valve block 14 is molded. The opposite, rounded end 35 of stiffener 34 bears against the extreme, proximal end of the root section 4 of implant cylinder 1. Apertures 42 formed in the conical segment 40 of stiffener 34 permit unimpeded fluid flow from reservoir chamber 12 into the valve chamber formed within valve block 14, and thence into distal end section 2 through valve seat or port 16. Stiffener 34 supports the flexible walls forming the proximal, reservoir portion 4 of cylinder 1 at all times. The strength and rigidity which stiffener 34 lends to proximal section 4 of the implant device particularly aids in the insertion of proximal section 4 within the root end of the corpora cavernosa of a male patient at the location shown in FIG. 5.

In the embodiment of the penile prosthesis shown in FIGS. 1-5, the proximal root section 4 of the implant cylinder 1 which serves as reservoir chamber 12 also functions as the pump means. The walls of cylinder 1 defining proximal section 4 are resiliently compressible inwardly. Thus, the application of external pressure to proximal section 4 will cause fluid to be expelled therefrom under pressure into distal section 2 through valve 16-18. As noted above, cylinder 1 is adapted to be surgically implanted within the corpus cavernosum of the penis. Although one implant cylinder 1 could be satisfactorily utilized, it is anticipated that two separate prosthetic implant cylinders 1 will be utilized, with one of such cylinders being implanted within each of the corpus cavernosum of the penis in the manner shown in FIG. 5. Such a double cylinder prosthetic system provides a measure of redundancy in case one cylinder should fail. The surgical procedure for implanting two of the cylinders 1 within the corpora cavernosa is substantially the same as that described in U.S. Pat. No. 3,954,102 with respect to the inflatable, prosthetic cylinders. Cylinders 1 are inserted into the corpora cavernosa through an incision made at the base of the penis. The corpora cavernosa regions of the penis are first dilated, as by the insertion of a metal rod through the incision to displace the erectile tissue and create a space for the subsequent insertion of the prosthetic cylinders 1. After insertion, distal end section 2 will extend within the pendulous portion of the penis, and proximal section 4 of the cylinder will extend into the root end of the corpora cavernosa as shown in FIG. 5. Proximal section 4 comprising the combined fluid reservoir and pump will be located within the root end of the corpora cavernosa at the location where it may be subjected to compression and pumping action by the application of manual pressure to the patient's perineal tissue. The arrow in FIG. 5 indicates the location and direction of the application of manual pressure to the perineum for compressing the walls of pump-reservoir section 4 of cylinder 1. Such a pressing action will force fluid under pressure from proximal, reservoir section 4 against valve poppet 18, thereby overcoming the pressure of spring 24 and displacing valve poppet 18 to an open position with respect to seat 16. Pressurized fluid is thus caused to flow from reservoir 12 into distal end section 2. The resultant rigidizing of distal section 2 under fluid pressure produces an erection. When it is desired to return the penis to a flaccid state, it is only necessary for the patient to apply pressure to valve section 6 of the implant device. This may be done by utilizing the thumb and forefinger to apply squeezing pressure to the tissue adjacent the base of the penis. The resultant squeezing action at the valve location defined by reinforcing band 28 will cause valve seat 16 to be compressed in one direction and elongated in the opposite direction as shown in FIG. 4. FIG. 3 illustrates the condition of the valve assembly in its normal, rest condition free from the application of any such squeezing pressure. The vertical deformation of valve seat 16 as illustrated in FIG. 4 results in the forming of openings 44 adjacent the top and bottom of valve poppet 18. Fluid flows from distal end section 2 of cylinder 1 through openings 44 back into reservoir chamber 12, thereby depressurizing distal end section 2 and causing it to collapse to the condition shown in FIG. 5. This permits the penis to return to the nonerect state of FIG. 5. The use of squeezing pressure to manipulate valves 16-18 to an open condition is substantially the same as that described for the bypass, squeeze valve in FIGS. 10-12 of U.S. Pat. No. 3,954,102. It is to be noted that valve section 6 of the penile prosthesis is positioned along cylinder 1 at such a location that it will be located substantially as shown in FIG. 5 adjacent the base end of the penis and just inwardly from the body plane of the patient where it will be accessible to squeezing pressure applied to the skin adjacent the base of the penis.

An alternative embodiment of the implantable penile prosthesis is shown in FIGS. 6–9. The implantable prosthetic cylinder 1 is substantially identical to that illustrated in FIGS. 1 and 2. Thus, the implantable prosthetic cylinder comprises a distal end section 2 which is pressurizable to assume a rigid condition, a proximal, root section 4 which serves as a fluid reservoir chamber 12, and a valve section 6 which may be conveniently located between the distal and root cylinder sections 2 and 4. Rather than utilizing the proximal section 4 of cylinder 1 as the pumping means, a separate elastomeric bulb 46 is employed as a pump device. Bulb 46 is sized to fit conveniently within the scrotal sac of the patient as illustrated in FIG. 6, and is connected to the valve section 6 by means of flexible and stretchable elastomeric tubing 48. Tubing 48 may be made out of the same silicone rubber utilized for pump bulb 46. Stretchable tube 48 serves as a fluid conduit connecting pump bulb 46 to a valve chamber 50 formed within a valve block 52 contained within implant cylinder 1. Valve block 52 is molded from solid rubber, preferably medical grade silicone in the same manner as is valve block 14 of the embodiment shown in FIGS. 1 and 2. Valve block 52 may also be located within cylinder 1 between reservoir chamber 12 of proximal section 4 and distal section 2 of the implant cylinder for convenient connection with pump bulb 46 through tube 48. As with the embodiment of FIGS. 1 and 2, valve section 6 may be reinforced by a band or ring 28 made of the same silicone or polyurethane material of which cylinder 1 is constructed. A stiffener 34 of the same shape and construction as illustrated and described above with respect to FIGS. 1 and 2 may also preferably be utilized to lend rigidity and strength to proximal, flexible wall reservoir section 4 of implant cylinder 1. Stiffener 34 is affixed to rubber valve block 52 and positioned within proximal section 4 of the implant cylinder in the same manner as described above with respect to FIGS. 1 and 2.

Since the reservoir chamber 12 for the pressurizing fluid is formed within proximal section 4 of the implant cylinder, pump bulb 46 need only function as a fluid transfer pump. Accordingly, pump bulb 46 is of a relatively small size, and may be implanted within the scrotal sac as shown in FIG. 6 without unduly interfering with bodily organs contained therein or causing discomfort to the patient. Pump bulb 46 is in fluid flow communication with reservoir chamber 12 and distal section 2 of the implant cylinder through conduit tube 48 and valve chamber 50. The flow of fluid between these components of the system is controlled by a valve mechanism positioned within valve block 52. A first check valve comprised of a valve seat 54 formed within valve block 50 and a valve poppet 56 controls flow between fluid reservoir chamber 12 and pump bulb 46. A valve stem 58 is slidably positioned within U-shaped poppet element 56 in slidable relation thereto. Stem 58 is normally urged to the left as viewed in FIG. 7 against poppet 56 to hold it in a closed position against valve seat 54 by a coil spring 60 bearing against stem collar 62. The opposite end of spring 60 bears against an annular shoulder 64 formed on valve block 52. Pressure differentials created across valve seat 54 by the pumping action of bulb 46 permit valve poppet 56 to be unseated only so as to permit fluid flow in a direction from reservoir chamber 12 through valve chamber 50 to pump bulb 46.

A second check valve comprised of valve seat 66 and valve head 68 controls the flow of fluid between valve chamber 50 and distal end section 2 of the implant cylinder. Valve seat 66 preferably takes the form of a ring molded integrally with valve block 52 and protruding laterally from one side thereof as shown in FIG. 7. Valve head 68 is normally held in seating engagement therewith by coil spring 60. Valve stem extension 70 on which valve head 68 is formed may be molded integrally with valve stem 58 or securely affixed thereto for shifting movement therewith in a longitudinal direction.

The valve assembly further includes means for manually manipulating the first and second check valves 54–56 and 66–68 to open positions to permit fluid flow from distal end section 2 back into fluid reservoir chamber 12. For this purpose, an elongated, flexible connector 72 is attached between valve stem 58 and stretchable tube 48. Flexible connection 72 may take the form of a dacron cord or a medical suture. At its upper end it is affixed to a sleeve 74 received within a recess 76 formed in the collar 62 of valve stem 58. The bottom end of connector cord 72 may be looped through the side wall of stretchable tube 48 and secured thereto by a knot as illustrated in FIGS. 7–9. A retention band 78 is affixed around stretchable tube 48 over the location of attachment of cord 72 thereto in order to secure and hold the bottom end of cord 72 in place. Band 78 may also be a ring of silicone rubber.

The prosthetic device illustrated in FIGS. 6–9 is implanted in substantially the same way as that described above with respect to the embodiment of FIGS. 1–5. Distal end section 2 of the implant cylinder 1 will be contained within one of the corpus cavernosum of the penis, and proximal, fluid reservoir section 4 thereof will be located within the root end of one of the corpus cavernosum. Pump bulb 46 is located within the scrotal sac as stated above. When the patient desires to achieve an erection, pumping action is applied to bulb 46 by applying squeezing pressure thereto through the scrotal sac. Repetitive, squeezing manipulation of pump bulb 46 in that manner will have the effect of transfering fluid from reservoir chamber 12 to distal end section 2 of the implant cylinder. As the walls of pump bulb 46 are released outwardly on the suction stroke of each pumping manipulation, valve poppet 56 will be drawn out of seating engagement with seat 54 and will shift to the right as viewed in FIG. 7 along valve stem 58. This permits fluid to flow from reservoir chamber 12, through valve chamber 52 and into pump bulb 46 through conduit 48. As the pump bulb is sequentially squeezed on the pumping stroke as illustrated in FIG. 8, the pressurized fluid within valve chamber 50 will force poppet 56 back to the left against seat 54. Simultaneously, the pressurized fluid acting on the underside of valve head 68 will shift it to the right as viewed in FIG. 8, overcoming spring pressure 60, to open valve seat 66. Fluid is thus permitted to flow under pressure into distal end section 2 of the implant cylinder. This causes flexible distal section 2 to elongate and rigidize as shown in FIG. 6 thereby producing an erection.

When it is desired to return the penis to a flaccid state, the patient manually exerts a downward, pulling action on pump bulb 46 through the walls of the scrotal sac. This has the effect of stretching tube 48 downwardly along its length and simultaneously pulling connecting cord 72 downwardly. Cord 72 will normally be slack when the valve mechanism is in the condition shown in FIG. 7. Downward pulling action on the connecting cord 72 through the aforesaid pulling manipulation of pump bulb 46 and stretchable tube 48 causes the valve assembly contained within valve block 52 to be canted or tipped to the open position shown in FIG. 9. When the valve stem 58-70 is displaced by pulling on cord 72, valve poppet 56 and valve head 68 will be angularly displaced to the canted positions shown in FIG. 9, thereby opening flow ports or valve seats 54 and 66. Thus, fluid is permitted to flow from distal end section 2 back into reservoir chamber 12 and into pump bulb 46.

As stated above, distal end section 2 of the implant cylinder 1 is made of flexible, medical grade material which will permit it to collapse and bend to the condition shown in FIG. 5. Distal end section 2 is also inflatable to the extent that it may be rigidized in a straight condition for producing an erection as illustrated in FIG. 6. The term "inflatable" as used herein is intended to mean a penile prosthesis of the type having a distal end section 2 which is flexibly bendable to permit the penis to assume a flaccid state, but which rigidizes upon being pressurized to produce an erection. The implant cylinder as disclosed herein may be made of silicone or polyurethane so that distal end section 2 is expandable in girth and length; or it may be made of materials which permit distal end section 2 to distend only to a limited extent. The latter type of cylinder has the advantage that it can be rigidized with a lesser volume of fluid. Such a limited distensible cylinder can be made of silicone or polyurethane reinforced by dacron fibers. The fiber reinforcing limits the ability of distal section 2 to distend. The fiber reinforced implant cylinder may be made in the same manner as the limited distensible fluid chamber of the implant cylinder described in the aforesaid copending U.S. application Ser. No. 108,124.

It will readily be appreciated that the implantable prosthetic cylinder as disclosed herein with its self-contained fluid reservoir chamber at one end thereof will greatly simplify surgical implant procedures. No separate, reservoir chamber containing fluid is required to be implanted within the patient at a location remote from the penis. The embodiment illustrated and described with respect to FIGS. 1-5 also eliminates the need for a separate pump bulb by utilizing the proximal reservoir chamber section of the implant cylinder as the pumping device. With respect to the embodiment of FIGS. 6-9, the utilization of a fluid reservoir chamber formed within the implant cylinder, and the containment of the valve mechanism within the implant cylinder itself, permits the separate pump bulb implanted within the scrotal sac to be of relatively small size.

It is anticipated that various changes may be made in the construction, shape and operation of the penile prosthetic devices as disclosed herein without departing from the spirit and scope of the invention as defined by the following claims.

What is claimed is:

1. An implantable penile prosthesis comprising:
at least one elongated cylinder adapted to be implanted within a patient's penis, said cylinder having a flexible and collapsible distal end section for implantation within the pendulous penis which is constructed to rigidize upon being filled with pressurizing fluid, and a proximal, rear end section adapted to be implanted within the root end of the penis;
a fluid reservoir chamber formed within said proximal, rear end section of said cylinder;
valve means contained within said cylinder for controlling the flow of fluid back and forth between said fluid reservoir chamber and said flexible distal end of said cylinder; and
the walls of said proximal, rear end section of said cylinder forming said fluid reservoir chamber being resiliently compressible inwardly and defining an elongated, generally cylindrical chamber of sufficient length to extend into the patient's perineum where it is located upon implantation of said cylinder within the penis whereby said fluid reservoir chamber also serves as a pump means, with the application of external, manual pressure by the patient to said fluid reservoir chamber through the skin in the perineal region serving to force fluid under pressure from said reservoir chamber through said valve means and into said flexible distal end section of said cylinder for rigidizing thereof.

2. An implantable penile prosthesis as defined in claim 1 wherein:
said valve means is located within said cylinder between said fluid reservoir chamber and said distal end section.

3. An implantable penile prosthesis as defined in claim 1 wherein:
said valve means is comprised of a valve element and a seat constructed and assembled in cooperative juxtaposition to each other in such a way that said valve element is displaced to an open position by pressurized fluid upon pressing the walls of said reservoir chamber inwardly, to thereby permit pressurized fluid to flow into said distal end section of said cylinder for penile erection.

4. An implantable penile prosthesis as defined in claim 3 wherein:
said valve seat is deformable by means of external manipulation through pressure applied to the penis to open a flow passage through said seat and around said valve element to permit the return flow of fluid from said distal end section of said cylinder to said reservoir chamber for returning the penis to a flaccid state.

5. An implantable penile prosthesis as defined in claim 1 wherein:
a rigid, stiffening element is positioned within said reservoir chamber to lend support thereto.

6. An implantable penile prosthesis as defined in claim 1 wherein:
said distal end section of said cylinder is an expandable, tubular section.

7. An implantable penile prosthesis as defined in claim 1 wherein:
said distal end section of said cylinder is a tubular section made of materials limiting its ability to distend under pressure.

8. An implantable penile prosthesis comprising:
at least one elongated cylinder adapted to be implanted within a patient's penis, said cylinder having a flexible and collapsible distal end section for implantation within the pendulous penis which is constructed to rigidize upon being filled with pressurizing fluid, and a proximal, rear end section adapted to be implanted within the root end of the penis;
a fluid reservoir chamber formed within said proximal, rear end section of said cylinder;

valve means contained within said cylinder for controlling the flow of fluid back and forth between said fluid reservoir chamber and said flexible distal end of said cylinder;

pump means manually operable to transfer fluid under pressure from said fluid reservoir chamber to said flexible distal end of said cylinder for achieving an erection, said pump means comprising an elastomeric bulb adapted to be implanted within the male scrotum, said pump bulb being in fluid flow communication with said fluid reservoir chamber and with said distal end section through said valve means, whereby pumping manipulation of said bulb transfers fluid under pressure from said reservoir chamber to said distal end section to achieve a penile erection; and said valve means comprises first check valve means between said reservoir chamber and said pump bulb for permitting flow only from said reservoir chamber to said pump bulb, and second check valve means between said pump bulb and said distal end section of said cylinder for permitting fluid flow only from said pump bulb to said distal end section.

9. An implantable penile prosthesis as defined in claim 8 wherein:

said prosthesis further comprises means for manually manipulating said first and second check valve means to open positions to permit fluid flow from said distal end section back into said reservoir chamber.

10. An implantable penile prosthesis as defined in claim 9 wherein:

said means for manually manipulating said check valve means comprises connector means between said pump bulb and said valve means, whereby manual manipulation of said pump bulb through the male scrotum actuates said valve means to move said first and second check valve means to said open positions.

11. An implantable penile prosthesis as defined in claim 10 wherein:

said connector means comprises a stretchable tube section between said valve means and said pump bulb serving as a fluid conduit, and an elongated, flexible connector attached between said valve means and said stretchable tube, whereby downward pulling action on said pump bulb through the scrotum causes said connector to actuate said valve means to move said first and second check valve means to said open positions.

12. An implantable penile prosthesis as defined in claim 8 wherein:

said valve means is positioned between said fluid reservoir chamber and said distal end section of said cylinder.

* * * * *